United States Patent
Beck et al.

(10) Patent No.: US 7,830,517 B2
(45) Date of Patent: Nov. 9, 2010

(54) FLOW SCHEMES FOR ENHANCED LIGHT-TARGET INTERACTION IN FLUIDIC CHANNELS

(75) Inventors: Markus Beck, Palo Alto, CA (US); Peter Kiesel, El Centro, CA (US); Michael Bassler, Erlangen (DE); Tobias Burgel, Freiburg (DE)

(73) Assignee: Palo Alto Research Center Incorporated, Palo Alto, CA (US)

( * ) Notice: Subject to any disclaimer, the term of this patent is extended or adjusted under 35 U.S.C. 154(b) by 273 days.

(21) Appl. No.: 12/205,730

(22) Filed: Sep. 5, 2008

(65) Prior Publication Data

US 2010/0060892 A1    Mar. 11, 2010

(51) Int. Cl.
*G01N 21/00*    (2006.01)
(52) U.S. Cl. ........................................ 356/432; 356/436
(58) Field of Classification Search ......... 356/244–246, 356/432–436
See application file for complete search history.

(56) References Cited

U.S. PATENT DOCUMENTS

| 7,268,868 | B2 | 9/2007 | Kiesel et al. |
| 7,727,769 | B2 * | 6/2010 | Fukuda .................... 436/149 |
| 2008/0003665 | A1 * | 1/2008 | Potyrailo et al. ......... 435/287.2 |
| 2008/0013877 | A1 | 1/2008 | Schmidt et al. |
| 2009/0048805 | A1 * | 2/2009 | Kaduchak et al. ........... 702/179 |

* cited by examiner

*Primary Examiner*—Michael P Stafira
(74) *Attorney, Agent, or Firm*—Blakely, Sokoloff, Taylor & Zafman, LLP

(57)    ABSTRACT

An embodiment is a fluidic channel to enhance light-target interaction. A first channel portion receives a first excitation light, an analyte flow, and a sheath flow. The analyte flow and the first excitation light are separated while in the first channel portion. The sheath flow flows on two sides or surrounds the analyte flow. A second channel portion has a first redirection structure to redirect the analyte flow by the sheath flow into the first excitation light at a first detection area.

25 Claims, 14 Drawing Sheets

FLOW SCHEMES FOR ENHANCED LIGHT-TARGET INTERACTION IN FLUIDIC CHANNELS

TECHNICAL FIELD

The presently disclosed embodiments are directed to the field of optical systems, and more specifically, to fluidic channels.

BACKGROUND

Optical methods for detecting biological and chemical analytes, such as absorption, fluorescence, and Raman spectroscopy, have a number of applications in detecting analytes in liquid, imaging fluorescing particles, microfluidic devices, optical sensors, and bio-agent detection.

Anti-resonant waveguides are effective for guiding light inside a liquid in a fluidic channel. It is especially useful for fluorescence excitation within fluidic channels since it enables efficient use of excitation light, excitation of large area/volume, and it provides excellent stray light suppression. However, due to the special geometry of an anti-resonant waveguide, the light coupling is complicated. Dependent upon the coupling parameter, a stable and homogeneous light distribution may be achieved when a certain coupling length in the liquid is exceeded, typically about 10-100 times the waveguide thickness. With regard to bleaching of the fluorescence signal, it is necessary that excitation of the analyte is mainly concentrated to the detection area. Any interaction between excitation light and analyte prior to the detection area typically reduces the performance due to attenuation of excitation light, e.g., absorption or scattering, enhanced stray light, bleaching of fluorophores, and light induced analyte modifications.

SUMMARY

One disclosed feature of the embodiments is an apparatus to enhance light-target interaction in a fluidic channel. A first channel portion receives a first excitation light, an analyte flow, and a sheath flow. The analyte flow and the first excitation light are separated while in the first channel portion. The sheath flow flows on two sides or surrounds the analyte flow. A second channel portion has a first redirection structure to redirect the analyte flow by the sheath flow into the first excitation light at a first detection area.

One disclosed feature of the embodiments is a method to enhance light-target interaction in a fluidic channel. A first excitation light, an analyte flow, and a sheath flow are received to go through a first channel portion. The analyte flow and the first excitation light are separated while in the first channel portion. The sheath flow flows on two sides or surrounds the analyte flow. The analyte flow is redirected by the sheath flow into the first excitation light at a first detection area using a first redirection structure of a second channel portion.

One disclosed feature of the embodiments is an apparatus to enhance light-target interaction in a fluidic channel. A first channel portion receives a first excitation light, an analyte flow, and a sheath flow. The analyte flow and the excitation light are aligned while in the first channel portion in an area. The sheath flow flows on two sides or surrounds the analyte flow. A second channel portion has a first redirection structure to redirect the analyte flow by the sheath flow out of the first excitation light away from the area.

BRIEF DESCRIPTION OF THE DRAWINGS

Embodiments may best be understood by referring to the following description and accompanying drawings that are used to illustrate embodiments. In the drawings.

DETAILED DESCRIPTION

Figure 1:
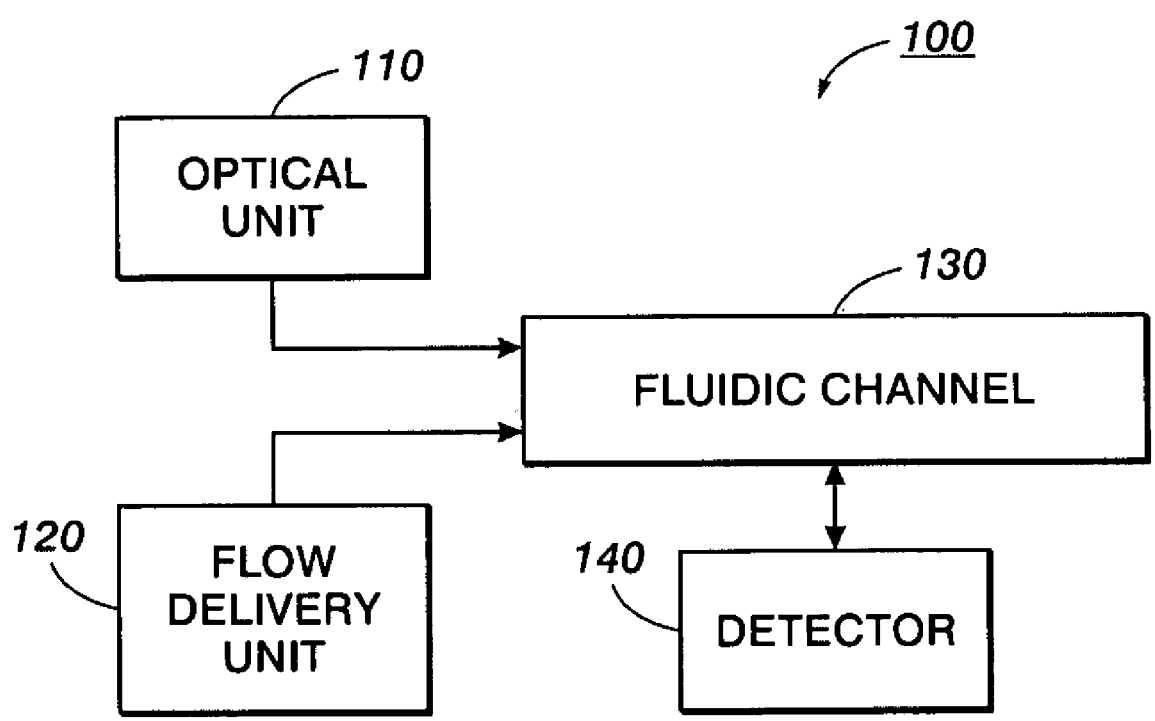
FIG. 1 is a diagram illustrating a system in which one embodiment may be practiced.

One disclosed feature of the embodiments is a technique to enhance, concentrate, or restrict light-target interaction in a fluidic channel. A first channel portion receives a first excitation light, an analyte flow, and a sheath flow. The analyte flow and the excitation light are separated while in the first channel portion. The sheath flow flows on two sides or surrounds the analyte flow. A second channel portion has a first redirection structure to redirect the analyte flow by the sheath flow into the first excitation light at a first detection area.

In another embodiment, the analyte flow and the excitation light are aligned while in the first channel portion in an area. The sheath flow flows on two sides or surrounds the analyte flow. A second channel portion has a first redirection structure to redirect the analyte flow by the sheath flow out of the first excitation light away from the area.

In the following description, numerous specific details are set forth. However, it is understood that embodiments of the invention may be practiced without these specific details. In other instances, well-known circuits, structures, and techniques have not been shown to avoid obscuring the understanding of this description.

One disclosed feature of the embodiments may be described as a process which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a program, a procedure, a method of manufacturing or fabrication, etc. One embodiment may be described by a schematic drawing depicting a physical structure. It is understood that the schematic drawing illustrates the basic concept and may not be scaled or depict the structure in exact proportions.

Embodiments may include three basic techniques: redirecting the analyte flow into an excitation or detection area, redirecting the analyte flow out of an excitation or detection area, and redirecting the analyte flow from one excitation or detection area to another different excitation or detection area. One embodiment is a technique to enhance, concentrate, or restrict the interaction between the excitation light and the target analyte in the detection area. The analyte may be a homogeneous medium (e.g., fluid) or particles in a medium. Any suitable medium or particles may be used. Examples of particles may include droplets, small volumes of segregated fluid, bubbles, single molecules, agglomerated molecules, molecule clusters, biological cells, viruses, bacteria, proteins, Deoxyribonucleic acid (DNA), microparticles, nanoparticles, and emulsions. The technique includes anti-resonantly coupling and guiding the excitation light within the sheath flow and using the sheath flow to redirect the analyte flow into the wave-guided excitation light at the detection area. This may be achieved by constructing a fluidic channel having a geometry or an additional flow path such that the excitation light and the analyte flow containing the analyte are separated before the detection area to avoid light-induced modifications of the analyte, bleaching of the native fluorescence or fluorescence dyes, or attenuation of the guided light due to light-target interaction. The analyte flow is then redirected into the excitation light at the detection area. In one embodiment, the geometry of the fluidic channel may also allow redirecting the analyte flow away from the guided light after the detection area to have a defined interaction length and prevent stray light. The analyte flow may also be redirected from one detection area to another detection area. The technique may use the sheath flow to redirect the analyte flow out of the wave-guided excitation light away from the detection area.

FIG. 1 is a diagram illustrating a system 100 in which one embodiment may be practiced. The system 100 includes an optical unit 110, a flow delivery unit 120, a fluidic channel 130, and a detector 140. It is contemplated that the system 100 may include more or less than the above elements.

The optical unit 110 may generate at least a light beam of excitation light. There may be one or more excitation lights. The optical unit 110 may include a light source and associated optics such as lens, mirrors, etc, to direct at least a light beam to the fluidic channel 130. In one embodiment, the light source may be a laser. The excitation light may be anti-resonantly guided in the fluidic channel 130.

The flow delivery unit 120 may include a flow delivery mechanism to deliver a sheath flow and an analyte flow to the fluidic channel 130. The analyte flow may carry a sample or target analyte that may be detected in the fluidic channel 130. There may also be mechanisms to reduce the pressure downstream. The flow delivery unit 120 may include a fluid and/or bias control mechanism to control the flow rate of the flows.

The fluidic channel 130 is coupled to the flow delivery and optically coupled to the optical unit to enhance the interaction between the excitation light and the analyte in the analyte flow in the fluidic channel 130. The fluidic channel 130 may have geometry configured to modulate, redirect, or deflect the analyte flow into the excitation light in a detection area, and out of the excitation light from the detection area, in the fluidic channel 130. The fluidic channel 130 may be implemented by glass material. It may be a continuous channel including sections or portions that are shaped in such a way to provide the redirection of the analyte flow into or out of the excitation light. The sections or portions of the fluidic channel 130 may be coupled by a redirection structure. The redirection structure may provide the necessary shape or geometry for the overall channel or include additional ports to accommodate bias flows that cause the redirection of the analyte flow. Several embodiments for the fluidic channel 130 may be available based on the structure of the redirection structure.

The detector 140 may include a processor or an optical array to detect light transmitted, output, or scattered by the target analyte in the detection area.

In the drawings shown in FIGS. 2 through 12, the lateral boundaries of the channel may be shown while the other two channel walls may be two parallel planes. By total internal reflection at the (outer) surface of these planar channel walls, anti-resonant wave-guiding may be possible. Accordingly, the described embodiments may assume parallel boundaries in the plane of the drawing and the described functionality may be achieved by shaping the shown boundaries between these parallel planes appropriately. Equivalent or similar functionalities may be achieved by variations of any of the channel boundaries.

Figure 2:
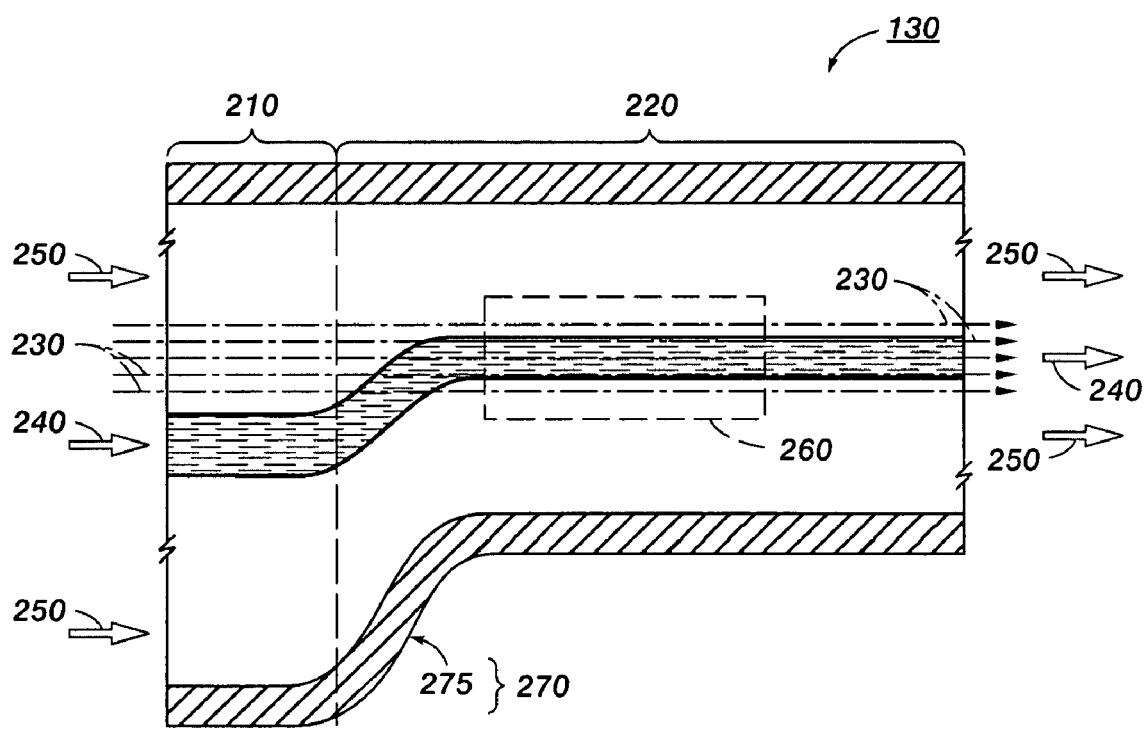
FIG. 2 is a diagram illustrating a fluidic channel with one deflection segment according to one embodiment.

FIG. 2 is a diagram illustrating the fluidic channel 130 shown in FIG. 1 with one deflection segment according to one embodiment. The fluidic channel 130 includes a first channel portion 210 and a second channel portion 220. The first channel portion 210 and the second channel portion 220 are integrated into a continuous channel.

The first channel portion 210 receives a first excitation light 230 of the light beam from the optical unit 110, an analyte flow 240, and a sheath flow 250. The analyte flow 240 and the first excitation light 230 are separated while in the first channel portion 210. The sheath flow 250 flows on two sides or surrounds the analyte flow 240. The sheath flow 250 may be a weakly absorbing flow. Since the analyte flow 240 and the first excitation light 230 are separated before reaching the detection area 260, the interaction between the light and the analyte in the analyte flow 240 is reduced, thus avoiding analyte modifications, bleaching, or light attenuation.

Figure 5:
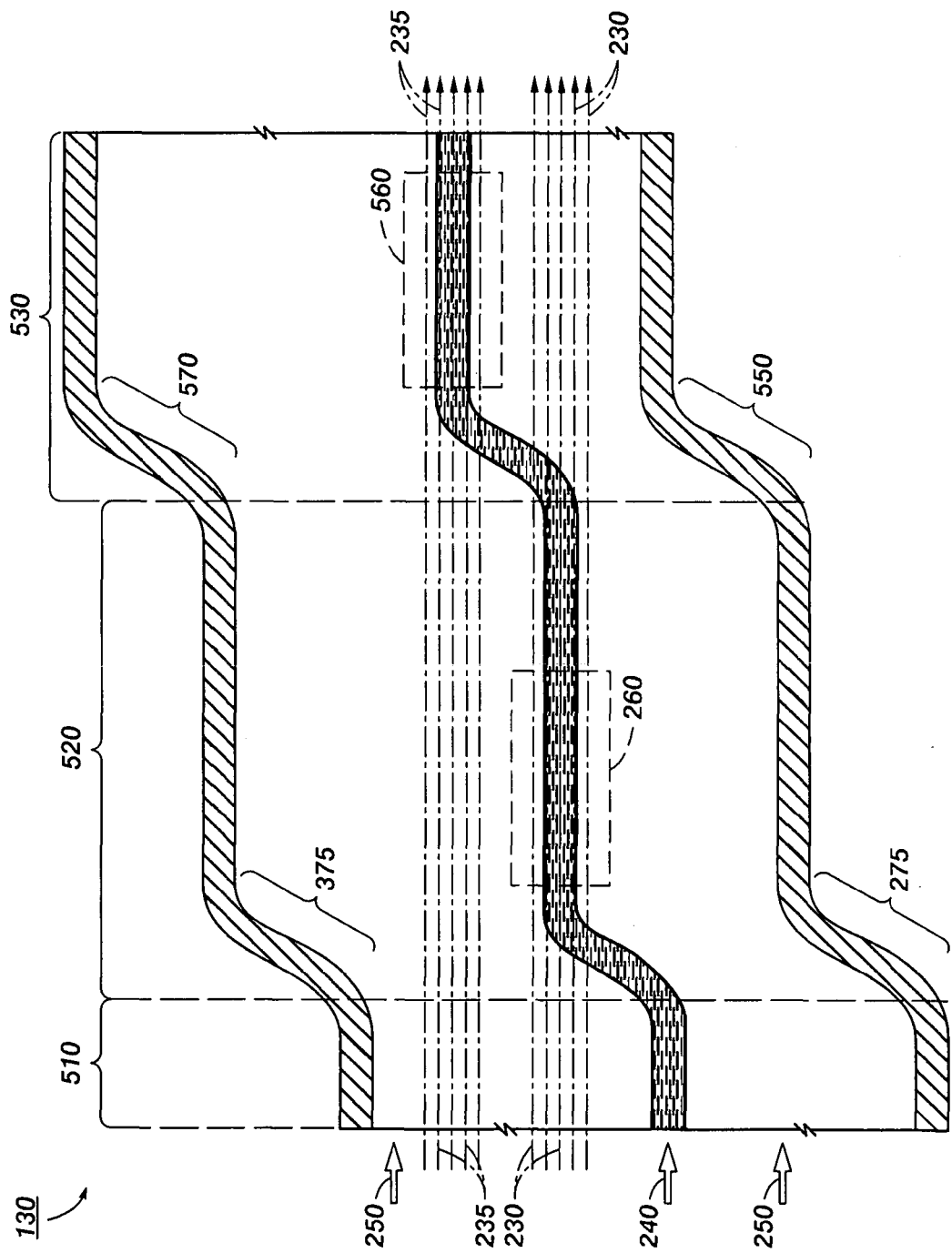
FIG. 5 is a diagram illustrating a fluidic channel having two detection areas with deflection segments according to one embodiment.
Figure 7:
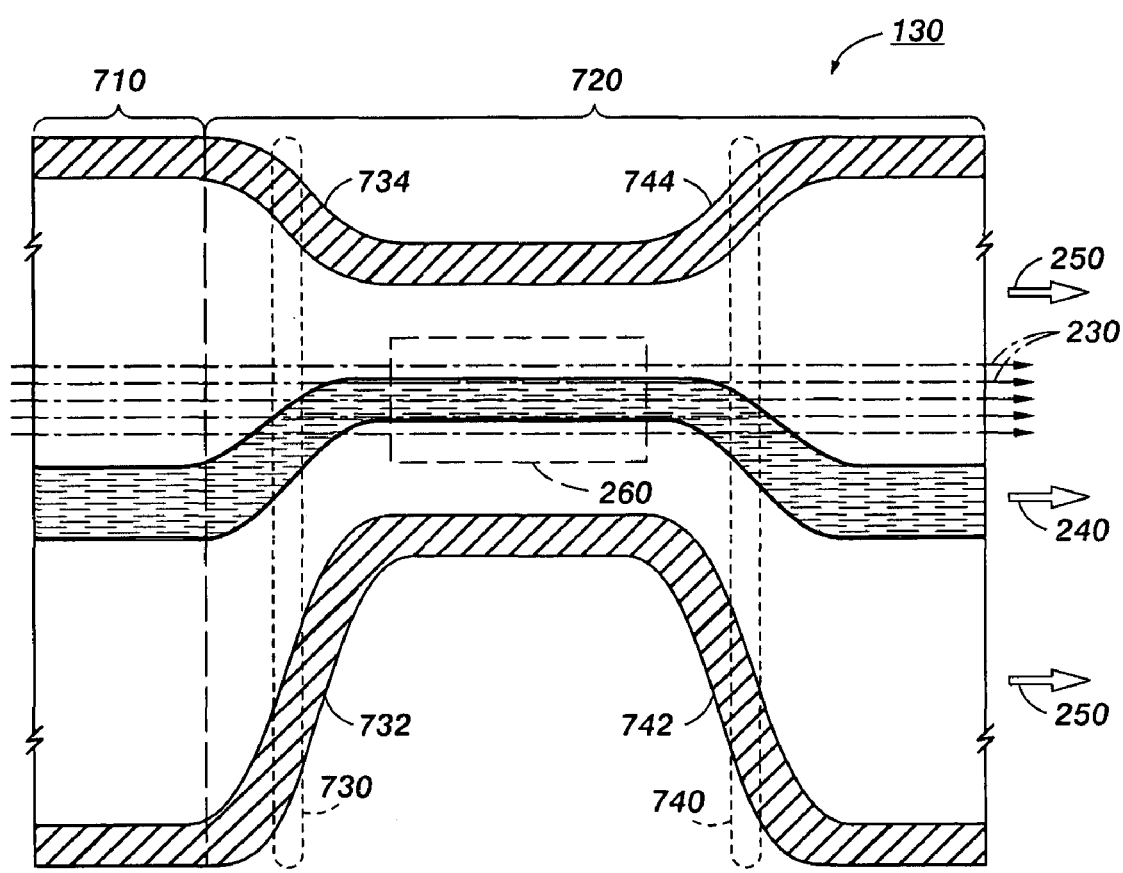
FIG. 7 is a diagram illustrating a fluidic channel with narrowing portion according to one embodiment.

The second channel portion 220 has a first redirection structure 270 coupled to the first channel portion 210 to redirect the analyte flow 240 by the sheath flow 250 into the first excitation light 230 at a first detection area 260. The first detection area 260 is the area where the detector 140 (FIG. 1) focuses on to detect the light. The first redirection structure 270 includes a first deflection segment 275 that is configured to connect a first side of the first channel portion 210 to a first side of the second channel portion 220. The first deflection segment 275 may have a curvature or deflection pattern that is designed or selected to affect the flow of the sheath flow 250. It causes the analyte flow 240 to be deflected by the sheath flow 250 into the first excitation light 230 at the first detection area 260. Within the first detection area 260, the analyte flow 240 and the excitation light 230 are aligned. Since the analyte flow 240 and the excitation light 230 are aligned and confined within the well defined detection area 260, the characterization of the analyte in the analyte flow 240 is improved. This characterization may include fluorescence detection, or determination of attenuation or absorption values as illustrated in FIG. 5 or FIG. 7.

Figure 3:
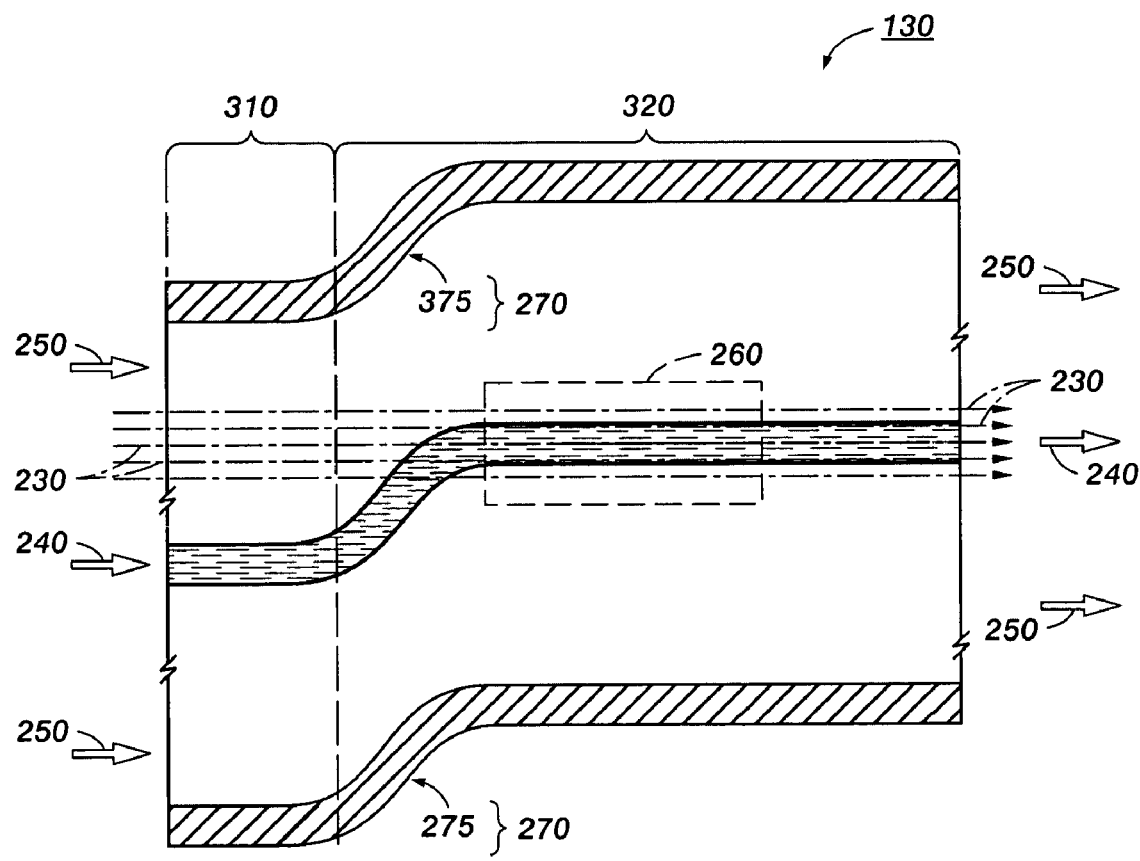
FIG. 3 is a diagram illustrating a fluidic channel with two deflection segments according to one embodiment.

FIG. 3 is a diagram illustrating the fluidic channel 130 shown in FIG. 1 with two deflection segments according to one embodiment. The fluidic channel 130 includes a first channel portion 310 and a second channel portion 320. The first channel portion 310 is similar to the first channel portion 210 shown in FIG. 2. The second channel portion 320 is similar to the second channel portion 220 shown in FIG. 2 except that the redirection structure 270 includes a second deflections segment 375 that connects a second side of the first channel portion 210 to a second side of the second channel portion 320.

The first and second deflection segments 275 and 375 cause the analyte flow 240 to be deflected by the sheath flow 250 into the first excitation light 230 at the first detection area 260. The curvatures of deflection patterns of the first and second deflection segments 275 and 375 may be the same or different, but in general they are in the same direction such that the combined effect is to deflect the analyte flow 240 into the first excitation light 230.

Figure 4:
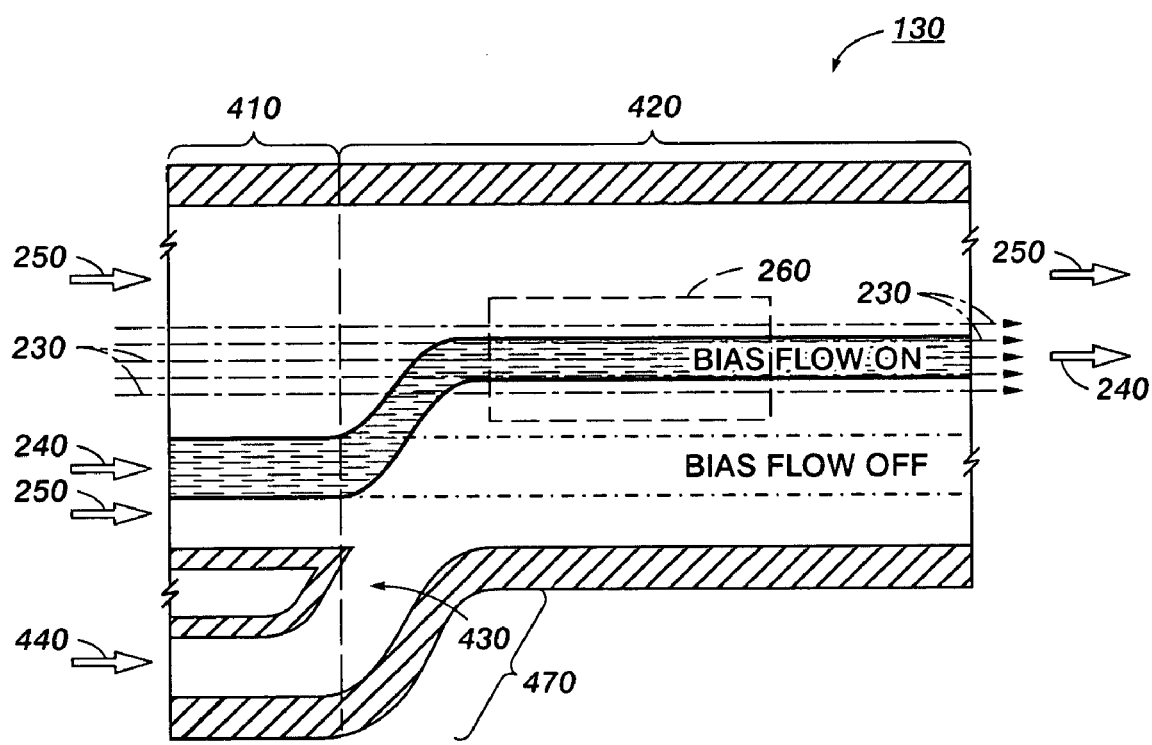
FIG. 4 is a diagram illustrating a fluidic channel with a bias port according to one embodiment.

FIG. 4 is a diagram illustrating the fluidic channel 130 shown in FIG. 1 with a bias port according to one embodiment. The fluidic channel 130 includes a first channel portion 410 and a second channel portion 420. The first channel portion 410 is similar to the first channel portion 210 shown in FIG. 2. The redirection structure in the second channel portion 420 includes a bias port 430 to receive or transport a bias flow 440 to flow through the second channel portion 420. The bias flow 440 causes the analyte flow 240 to be deflected into the first excitation light 230 at the first detection area 260. The flow rate of the bias flow 440 may be controlled by a bias control mechanism in the flow delivery unit 120 (FIG. 1). Since the flow rate of the bias flow 440 may be controlled dynamically, the redirecting of the analyte flow 240 may be carried out dynamically. When the bias flow 440 is turned off by the bias control mechanism (e.g., when the flow rate is zero), the analyte flow 240 is not redirected or deflected. It maintains the same flow direction. When the bias flow 440 is turned on by the bias control mechanism, the analyte flow 240 may be deflected into the first excitation light 230. It is also noted that when vacuum is used in the flow delivery unit 120 to control the bias flow 440, the bias flow 440 may be directed outward of the fluidic channel 130.

FIG. 5 is a diagram illustrating the fluidic channel 130 shown in FIG. 1 having two detection areas with deflection segments according to one embodiment. The fluidic channel 130 includes a first channel portion 510, a second channel portion 520, and a third channel portion 530. In this embodiment, a second excitation light 235 provides for a second excitation and detection. This embodiment extends the embodiment shown in FIG. 3 to include a second detection area 560. The analyte in the analyte flow 240 is guided through two distinct excitation regions sequentially.

The first and second channel portions 510 and 520 are similar to the first and second channel portions 310 and 320, respectively, shown in FIG. 3.

The third channel portion 530 has a second redirection structure coupled to the second channel portion to redirect the analyte flow 240 by the sheath flow 250 into the second excitation light 235 at the second detection area 560. The second redirection structure includes the deflection segments 550 and 570 that are similar to the deflection 275 and 375, respectively.

Figure 6:
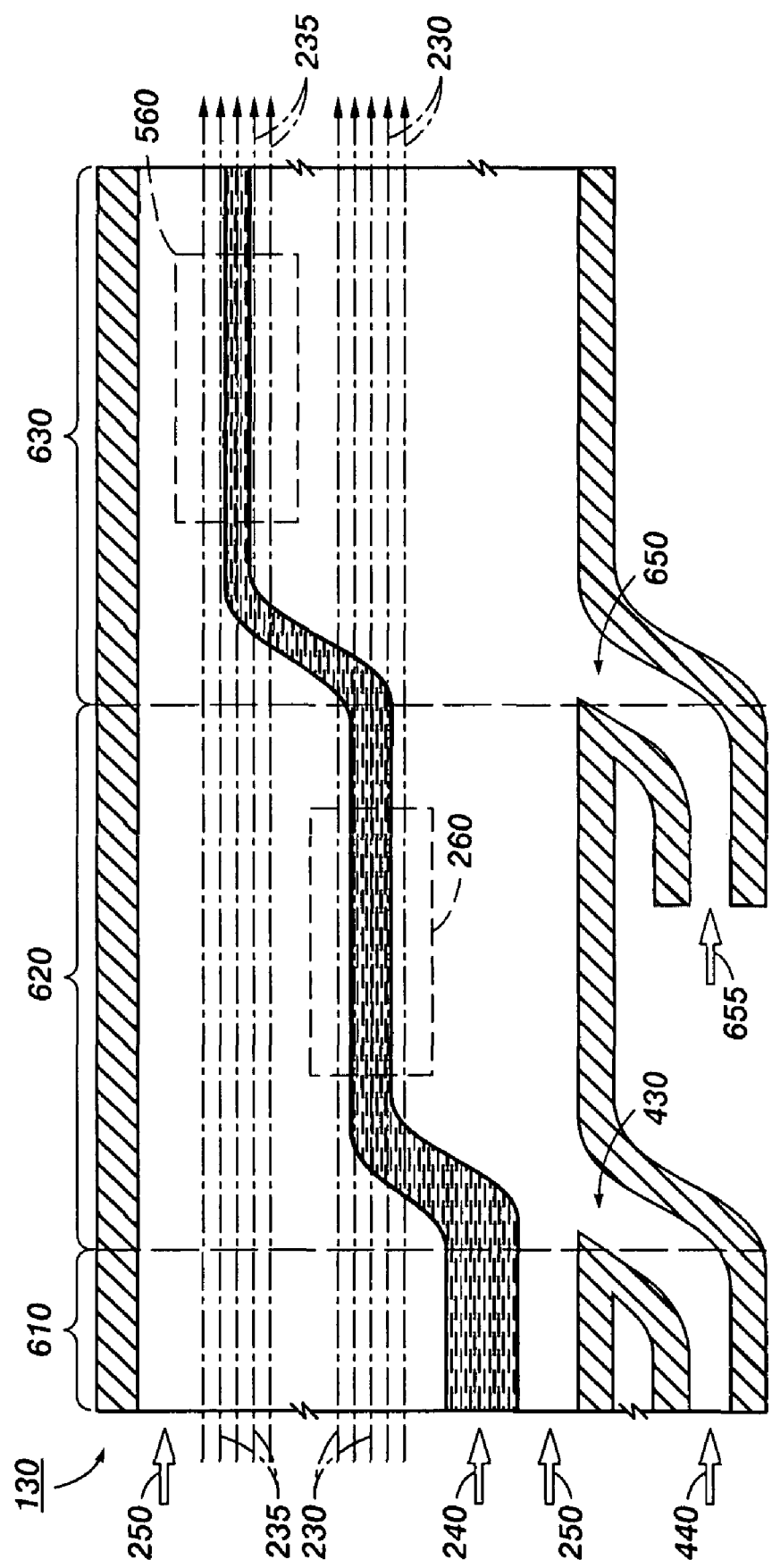
FIG. 6 is a diagram illustrating a fluidic channel having two detection areas with bias ports according to one embodiment.

FIG. 6 is a diagram illustrating the fluidic channel 130 shown in FIG. 1 having two detection areas with bias ports according to one embodiment. The fluidic channel 130 includes a first channel portion 610, a second channel portion 620, and a third channel portion 630. In this embodiment, a second excitation light 235 provides for a second excitation and detection. This embodiment extends the embodiment shown in FIG. 4 to include a second detection area 560. The analyte in the analyte flow 240 is guided through two distinct excitation regions sequentially.

The first and second channel portions 610 and 620 are similar to the first and second channel portions 410 and 420, respectively, shown in FIG. 3.

The third channel portion 630 has a second redirection structure coupled to the second channel portion to redirect the analyte flow 240 by the sheath flow 250 into the second excitation light 235 at the second detection area 560. The second redirection structure includes a bias port 650 to receive or transport a bias flow 655. The bias flow 655 causes the analyte flow 240 to be deflected into the second excitation light 235 at the second detection area 560.

Since the bias flows 440 and 655 may be dynamically turned on and off, this embodiment may be used to allow triggering the bias flow 655 to redirect the analyte flow 240 depending on the detected or measured result obtained from the first detection area 260. The second detection area 260 may be used as a special treatment for certain particles; for example, to selectively destroy pathogenic organisms with ultraviolet (UV) light. The bias flow 440 or 655 is different than the sheath flow 250 in that the bias flow (inlet or outlet) allows to control the position of a particle in a section of the fluidic channel 130 without affecting the position of the particles upstream. The bias flow 655, therefore, may be used as a consequence of, or conditionally on, a certain trigger signal generated in the first detection area 260 as discussed above.

FIG. 7 is a diagram illustrating the fluidic channel 130 shown in FIG. 1 with narrowing portion according to one embodiment. The fluidic channel 130 includes a first channel portion 710 and a second channel portion 720. The first channel portion 710 is similar to the first channel portion 210 shown in FIG. 2. The second channel portion 720 includes a first redirection structure 730 and a second redirection structure 740. The first redirection structure 730 includes first and second deflection segments 732 and 734. The first and second deflection segments 732 and 734, and the first and second deflection segments 742 and 744 are in opposite directions such that the second channel portion 720 is narrower than the first channel portion 710.

The second redirection structure 740 includes first and second deflection segments 742 and 744, and is located opposite of the first redirection structure 730 to redirect the analyte flow 240 by the sheath flow 250 out of the excitation light 230 away from the first detection area 260.

The fluidic channel 130 may narrow the flow channel of the second channel portion 720 in the detection area 260, which may be used to reduce or minimize the overall flow resistance for given dimensions of the detection area, as the highest resistance occurs in the narrow region in the detection area. A narrow detection area may be desired for two reasons. First, it is desired to focus the analyte flow or the stream of the particles in the flow as tightly as needed (not shown in FIG. 7). Second, at the same time, it is advantageous to reduce or minimize the amount of sheath liquid needed. In addition, the reduction of the total flow resistance of the device reduces or minimizes the required force and power to achieve certain flow speeds and flow rates. Particle focusing is beneficial to precisely control the particle position with respect to the excitation light, so that all particles are excited with the same intensity. Moreover, additional focusing enlarges the mean particle distance in flow direction, which might be needed to ensure characterization of individual particles even at high particle concentrations. This design results in an asymmetric narrowing of the channel as shown in FIG. 7.

It is noted that enhancing the light-target interaction with anti-resonant waveguides by guiding the light in the analyte-containing fluid is not restricted to sensors based on fluorescence detection. It may, for example, also be used for on-chip absorption detection. By directing the analyte flow in and out of a detection area, as shown in FIG. 5 (e.g., the first detection area 260) and FIG. 7, a well defined interaction length for an attenuation or absorption measurement may be created.

The configuration of the fluidic channel 130 may be modified or extended based on the basic configurations shown in FIG. 2 through FIG. 7. For example, more than two detection areas may be provided. In addition, techniques for deflecting or redirecting the analyte flow 240 at the detection areas may be the same or different. When the bias flow is used, it may be into or out of the channel. Furthermore, bias flows at the same channel position may be at opposite sides. Moreover, a bias flow may be sideways, upward, or downward or in any direction. Several embodiments illustrating these configurations are shown in FIGS. 8 through 12. In these illustrative embodiments, the fluidic channel 130 includes first, second, and third channel portions 810, 820, and 830, respectively. The second and third channel portions 820 and 830 have first and second detection areas 850 and 860, respectively.

Figure 8:
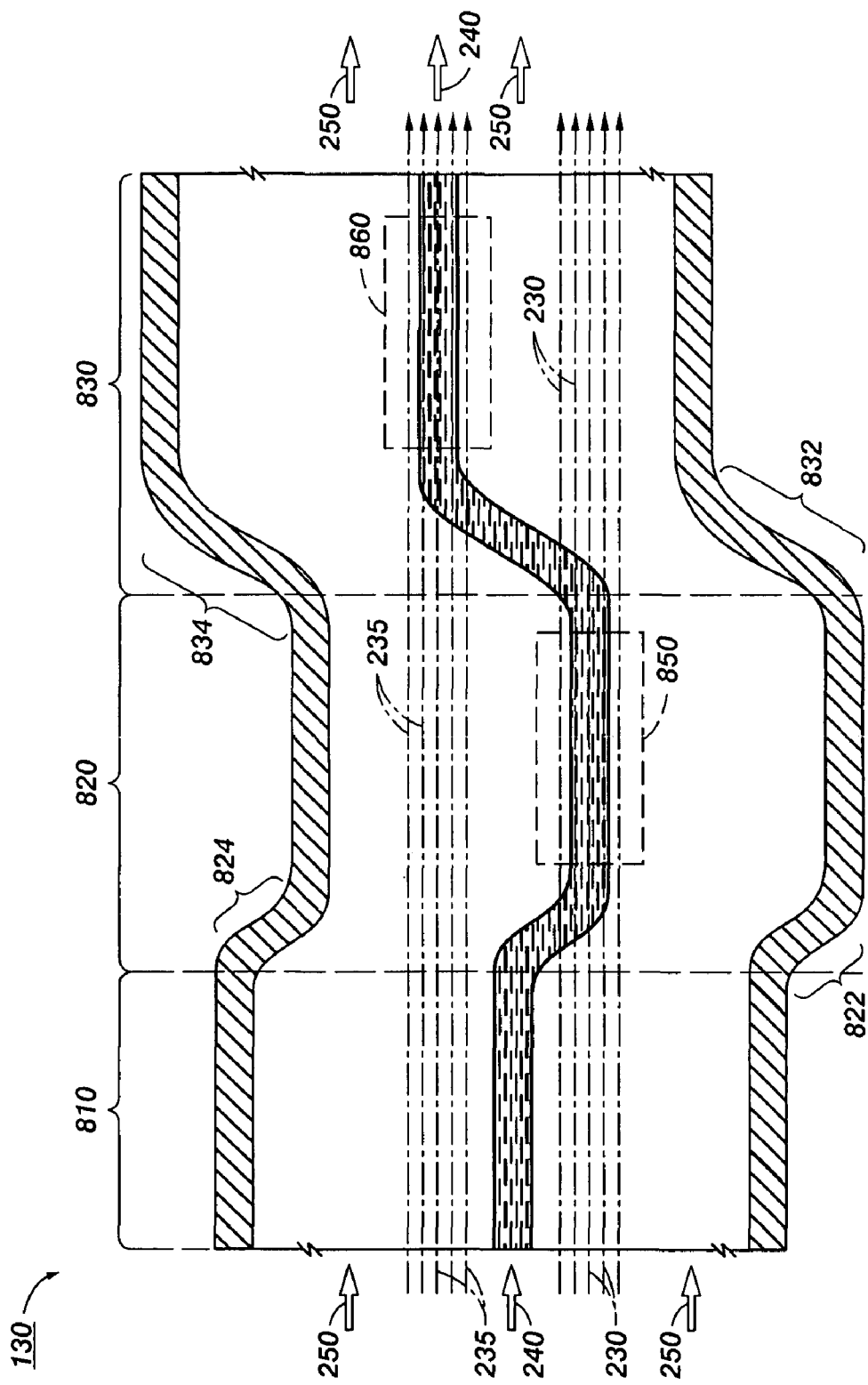
FIG. 8 is a diagram illustrating a fluidic channel with up and down channel portions according to one embodiment.

FIG. 8 is a diagram illustrating the fluidic channel 130 with up and down channel portions according to one embodiment. The redirection structure of the second channel portion 820 includes deflection segments 822 and 824. The redirection structure of the third channel portion 830 includes deflection segments 832 and 834. The deflection segments 822 and 824 are in an opposite direction of the deflection segments 832 and 834 such that the analyte flow 240 is deflected or redirected up and down as it flows through the channel.

Figure 9:
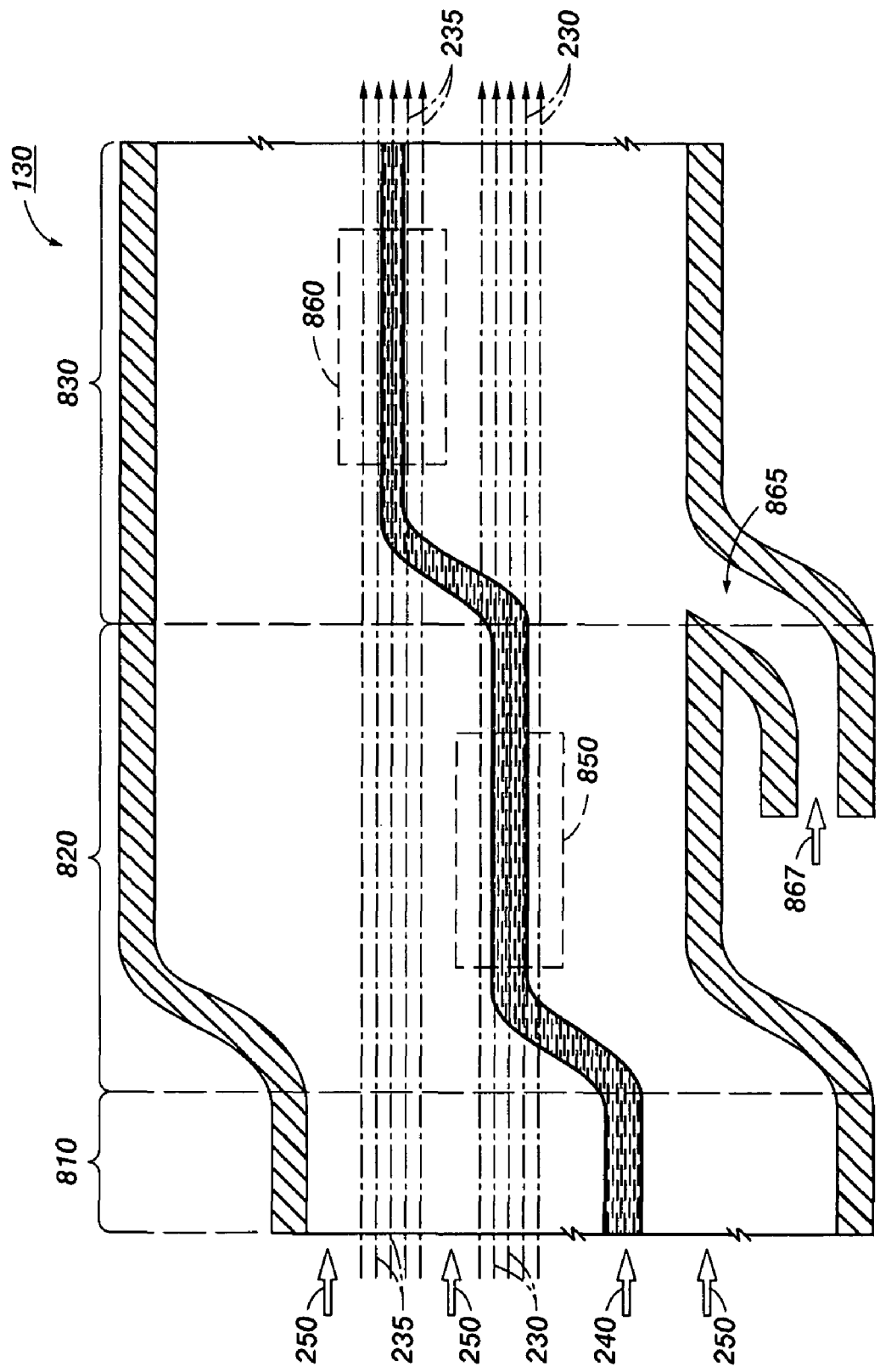
FIG. 9 is a diagram illustrating a fluidic channel with a combination of deflection segments and bias flow according to one embodiment.

FIG. 9 is a diagram illustrating the fluidic channel 130 with a combination of deflection segments and bias flow according to one embodiment. The redirection structure in the second channel portion 820 includes deflection segments while the redirection structure in the third channel portion 830 includes a bias port 865 to transport a bias flow 867.

Figure 10:
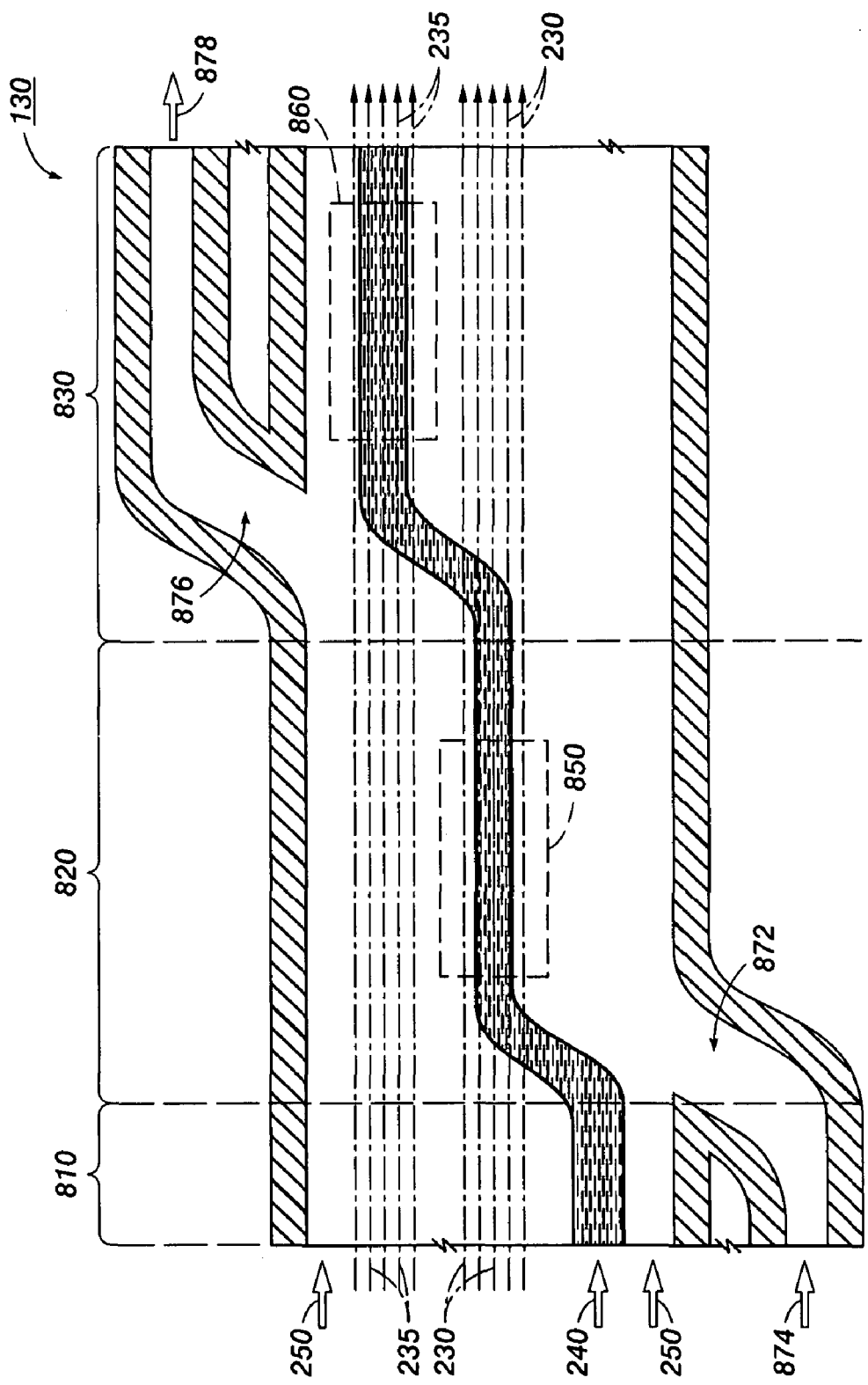
FIG. 10 is a diagram illustrating a fluidic channel with in and out bias flows at different channel portions according to one embodiment.

FIG. 10 is a diagram illustrating the fluidic channel 130 with in and out bias flows at different channel portions according to one embodiment. The second channel portion 820 includes a bias port 872 to transport a bias flow 874 that flows into the channel. The third channel portion 830 includes a bias port 876 to transport a bias flow 878 that flows out of the channel.

Figure 11:
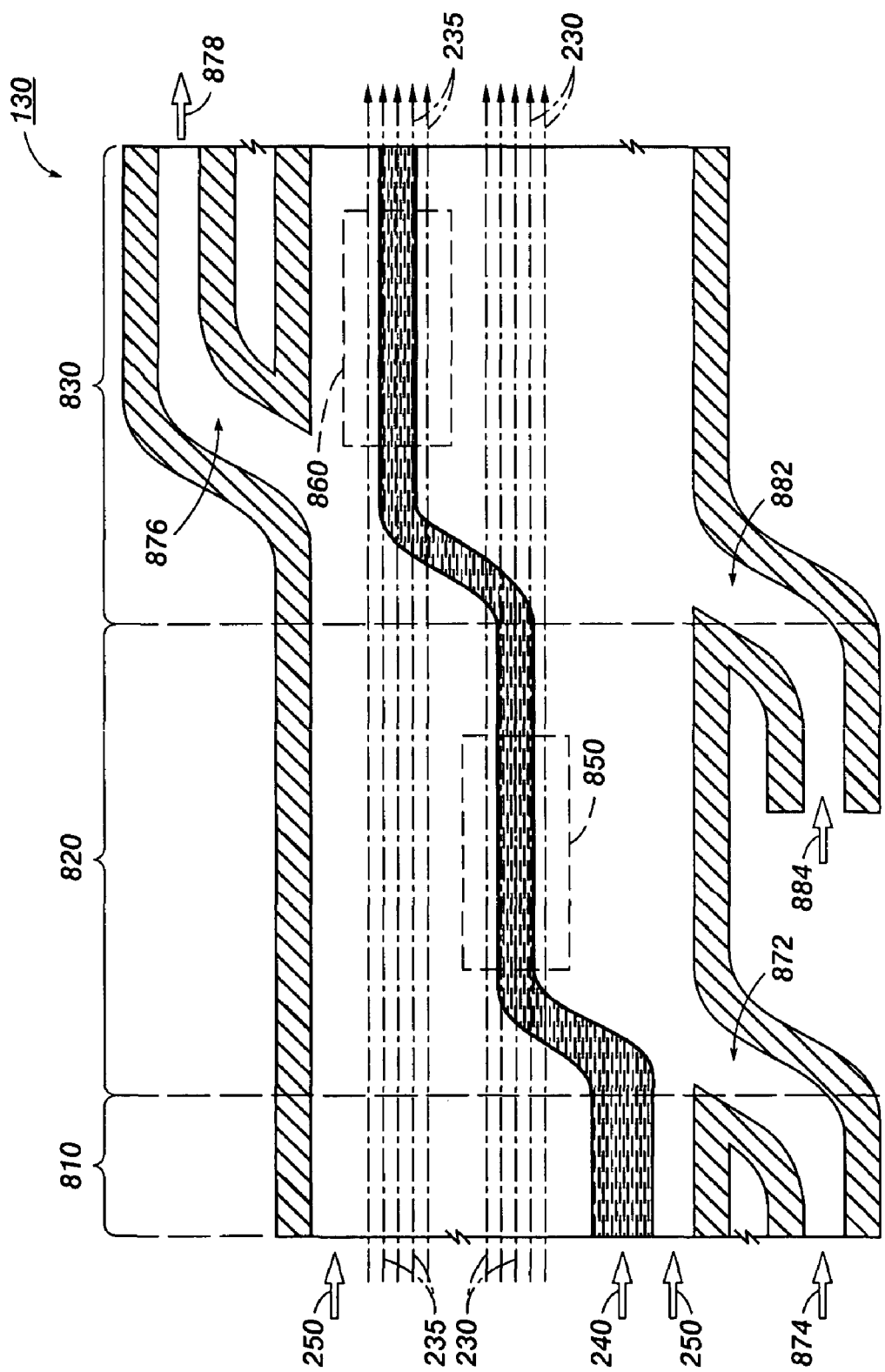
FIG. 11 is a diagram illustrating a fluidic channel with in and out bias flows at opposite sides of the same channel portion according to one embodiment.

FIG. 11 is a diagram illustrating the fluidic channel 130 with in and out bias flows at opposite sides of the same channel portion according to one embodiment. The second channel portion 820 includes a bias port 872 to transport a bias flow 874 that flows into the channel. The third channel portion 830 includes a bias port 882 to transport a bias flow 884 that flows into the channel and the bias port 876 to transport the bias flow 878 that flows out of the channel. The use of the two bias ports at the same channel portion may keep the flow speed of the analyte flow 240 approximately constant.

Figure 12:
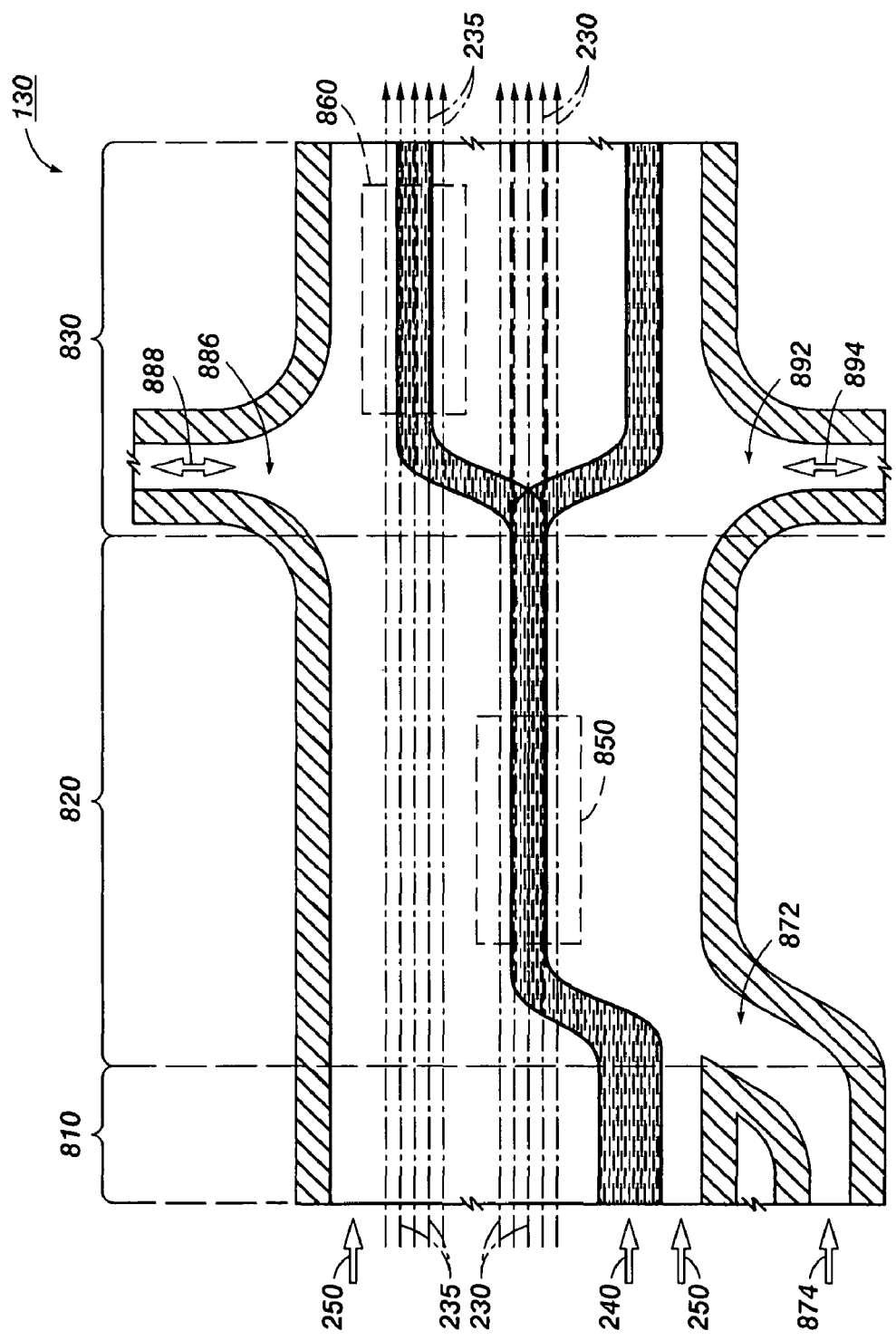
FIG. 12 is a diagram illustrating a fluidic channel with bias flows of different directions according to one embodiment.

FIG. 12 is a diagram illustrating the fluidic channel 130 with bias flows of different directions according to one embodiment. The second channel portion 820 includes a bias port 872 to transport a bias flow 874 that flows into the channel. The third channel portion 830 includes a bias port 892 to transport a bias flow 894 that flows into or out of the channel in the up or down direction and a bias port 886 located on the opposite side of the bias port 892 to transport a bias flow 888 that flows into or out of the channel in the up or down direction.

It is noted that that the terms "first", "second", and "third", etc. are used merely to distinguish the different sections of an embodiment. Embodiments may include a portion of any of the embodiments described above. The designations "first", "second", and "third", etc. may then be changed accordingly. For example, an embodiment may include the second channel portion 520 and the third channel portion 530 in FIG. 5. In that case, the designation "second channel portion 520" and "third channel portion 530" may become "first channel portion 520" and "second channel portion 530". In such an embodiment, the first channel portion 520 receives the first excitation light 230, the analyte flow 240, and the sheath flow 230 where the analyte flow 240 and the first excitation light 230 are aligned or merged while in the first channel portion 520 in the area 260. The sheath flow 250 flows on two sides or surrounds the analyte flow 240. The second channel portion 530 has a first redirection structure (e.g., deflection segments 550 and 560) coupled to the first channel portion 520 to redirect the analyte flow 240 by the sheath flow 250 out of the first excitation light 230 away from the area 260.

Figure 13:
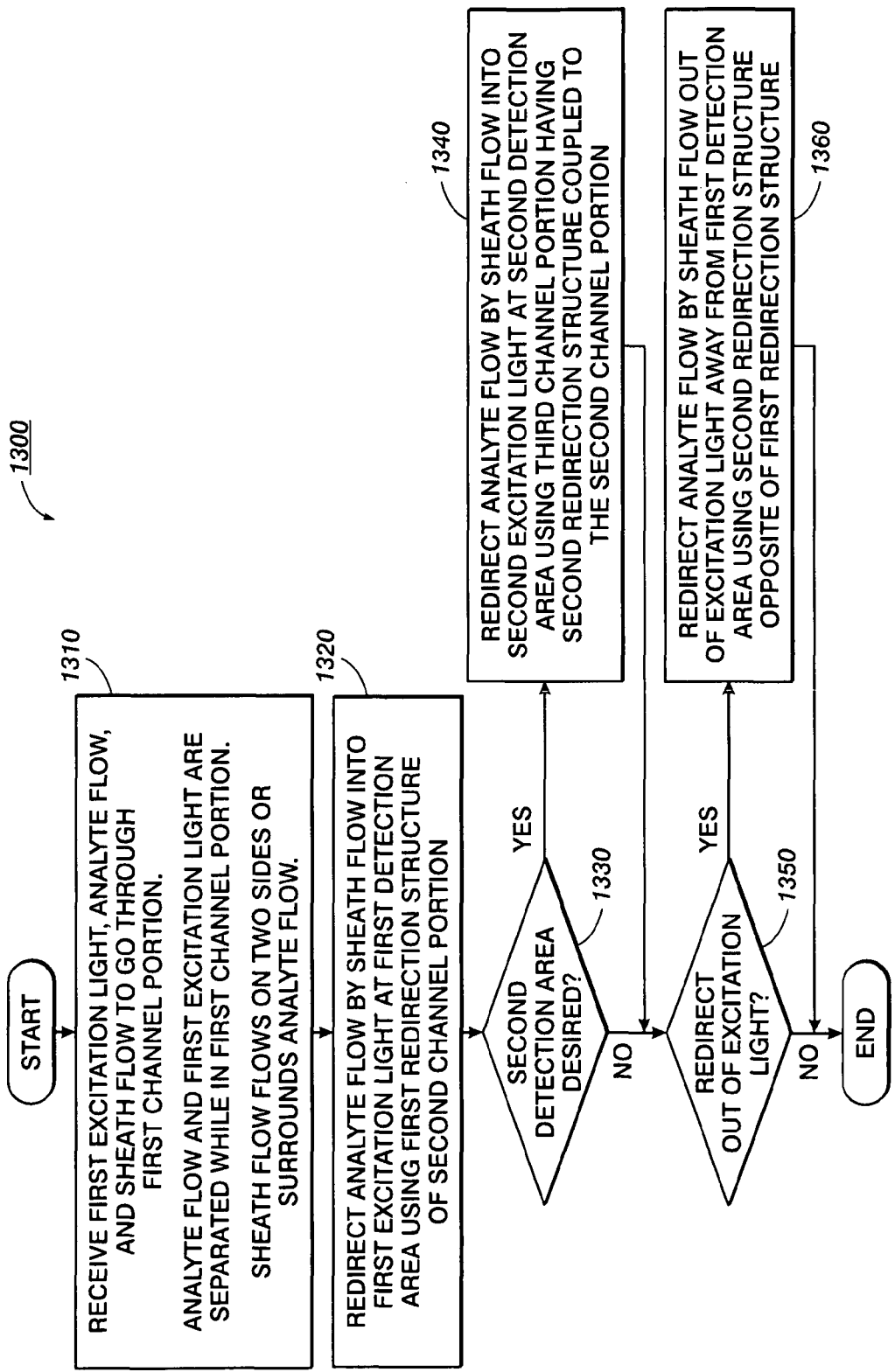
FIG. 13 is a flowchart illustrating a process to enhance light-target interaction according to one embodiment.

FIG. 13 is a flowchart illustrating a process 1300 to enhance light-target interaction according to one embodiment.

Upon START, the process 1300 receives a first excitation light, an analyte flow, and a sheath flow to go through a first channel portion (Block 1310). The analyte flow and the first excitation light are separated while in the first channel portion. The sheath flow flows on two sides or surrounds the analyte flow. Next, the process 1300 redirects the analyte flow by the sheath flow into the first excitation light at a first detection area using a first redirection structure of a second channel portion (Block 1320).

Then, the process 1300 determines if a second detection area is desired (Block 1330). If not, the process 1300 goes to block 1350. Otherwise, the process 1300 redirects the analyte flow by the sheath flow into a second excitation light at a second detection area using a third channel portion having a second redirection structure coupled to the second channel portion (Block 1340). Next, the process 1300 determines if it is desired to redirect the analyte flow out of the excitation light (Block 1350). If no, the process 1300 is terminated. Otherwise, the process 1300 redirects the analyte flow by the sheath flow out of the excitation light away from the first detection area using a second redirection structure opposite of the first redirection structure (Block 1360) and is then terminated.

Figure 14:
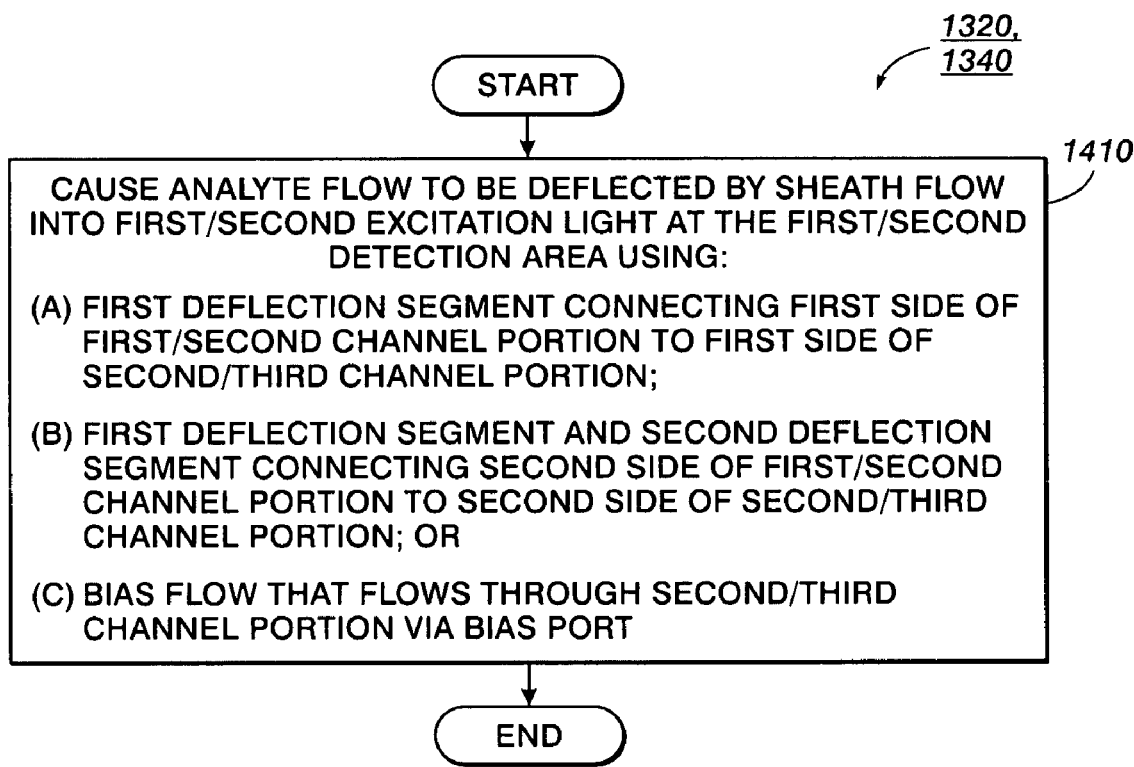
FIG. 14 is a flowchart illustrating a process to redirect the analyte flow into the excitation light according to one embodiment.

FIG. 14 is a flowchart illustrating the process 1320/1340 shown in FIG. 13 to redirect the analyte flow into the excitation light according to one embodiment.

Upon START, the process 1320/1340 causes the analyte flow to be deflected by the sheath flow into the first/second excitation light at the first detection area (Block 1410) using one of the following: (a) a first deflection segment connecting a first side of the first/second channel portion to a first side of the second/third channel portion, (b) the first deflection segment and a second deflection segment connecting a second side of the first/second channel portion to a second side of the second/third channel portion; and (c) a bias flow that flows through the second/third channel portion via a bias port. The process 1320/1340 is then terminated.

Embodiments include the construction of the fluidic channel to have various geometries or bias ports to enhance, concentrate, or restrict the light and target interaction. This may be achieved by causing the analyte flow or particle flow to be redirected into the excitation light at the detection area, or out of the excitation light away from the detection area. The construction of the fluidic channel has a number of novel aspects. First, the separation of the analyte from the excitation light before entering the detection zone helps to reduce problems associated with photo bleaching of the fluorescence, and scattering and absorption of excitation light. Also light-induced modifications of the analyte prior to entering the detection area are reduced. This may be useful in combination with anti-resonant waveguiding since the light is coupled into the detection area through the liquid and a certain minimum coupling length is required in order to reach a homogenous light distribution in the waveguide. Second, sheath flow fluid usually includes water or other weakly/non-absorbing buffer solution. Coupling and guiding light in the sheath flow consequently reduces the attenuation of the excitation light before reaching the detection area. This enables higher excitation and reduces problems associated with stray light. Third, analyte flow may be actively controlled to direct it through multiple parallel excitation areas subsequently. The active control may be used to choose a refined characterization or particle treatment based on a trigger signal generated in an upstream detection area.

The above description describes embodiments with anti-resonant wave-guiding. It is noted that embodiments may use a channel material with a refractive index that is lower than that of the fluid with conventional wave-guiding.

Elements of one embodiment may be implemented by hardware, firmware, software or any combination thereof. The term hardware generally refers to an element having a physical structure such as electronic, electromagnetic, optical, electro-optical, mechanical, electromechanical parts, etc. A hardware implementation may include analog or digital circuits, devices, processors, applications specific integrated circuits (ASICs), programmable logic devices (PLDs), field programmable gate arrays (FPGAs), or any electronic devices. The term software generally refers to a logical structure, a method, a procedure, a program, a routine, a process, an algorithm, a formula, a function, an expression, etc. The term firmware generally refers to a logical structure, a method, a procedure, a program, a routine, a process, an algorithm, a formula, a function, an expression, etc., that is implemented or embodied in a hardware structure (e.g., flash memory, ROM, EPROM). Examples of firmware may include microcode, writable control store, micro-programmed structure. When implemented in software or firmware, the elements of an embodiment are essentially the code segments to perform the necessary tasks. The software/firmware may include the actual code to carry out the operations described in one embodiment, or code that emulates or simulates the operations.

All or part of an embodiment may be implemented by various means depending on applications according to particular features, functions. These means may include hardware, software, or firmware, or any combination thereof. A hardware, software, or firmware element may have several modules coupled to one another. A hardware module is coupled to another module by mechanical, electrical, optical, electromagnetic or any physical connections. A software module is coupled to another module by a function, procedure, method, subprogram, or subroutine call, a jump, a link, a parameter, variable, and argument passing, a function return, etc. A software module is coupled to another module to receive variables, parameters, arguments, pointers, etc. and/or to generate or pass results, updated variables, pointers, etc. A firmware module is coupled to another module by any combination of hardware and software coupling methods above. A hardware, software, or firmware module may be coupled to any one of another hardware, software, or firmware module. A module may also be a software driver or interface to interact with the operating system running on the platform. A module may also be a hardware driver to configure, set up, initialize, send and receive data to and from a hardware device. An apparatus may include any combination of hardware, software, and firmware modules.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus comprising:
a first channel portion receiving a first excitation light, an analyte flow, and a sheath flow, the analyte flow and the first excitation light being separated while in the first channel portion, the sheath flow flowing on two sides or surrounding the analyte flow; and
a second channel portion having a first redirection structure coupled to the first channel portion to redirect the analyte flow by the sheath flow into the first excitation light at a first detection area.

2. The apparatus of claim 1 wherein the first redirection structure comprises:
a first deflection segment connecting a first side of the first channel portion to a first side of the second channel portion, the first deflection segment causing the analyte flow to be deflected by the sheath flow into the first excitation light at the first detection area.

3. The apparatus of claim 2 wherein the first redirection structure further comprises:
a second deflection segment connecting a second side of the first channel portion to a second side of the second channel portion, the first and second deflection segments causing the analyte flow to be deflected by the sheath flow into the first excitation light at the first detection area.

4. The apparatus of claim 1 wherein the first redirection structure comprises:
a bias port to receive a bias flow to flow through the second channel portion, the bias flow causing the analyte flow to be deflected into the first excitation light at the first detection area.

5. The apparatus of claim 1 further comprising:
a third channel portion having a second redirection structure coupled to the second channel portion to redirect the analyte flow by the sheath flow into a second excitation light at a second detection area.

6. The apparatus of claim 5 wherein the second redirection structure comprises:
a first deflection segment connecting a first side of the second channel portion to a first side of the third channel portion, the first deflection segment causing the analyte flow to be deflected by the sheath flow into the second excitation light at the second detection area.

7. The apparatus of claim 6 wherein the second redirection structure further comprises:
a second deflection segment connecting a second side of the second channel portion to a second side of the third channel portion, the first and second deflection segments causing the analyte flow to be deflected by the sheath flow into the second excitation light at the second detection area.

8. The apparatus of claim 5 wherein the second redirection structure comprises:
a bias port to receive a bias flow to flow through the third channel portion, the bias flow causing the analyte flow to be deflected into the second excitation light at the second detection area.

9. The apparatus of claim 3 wherein the first and second segments are in opposite directions such that the second channel portion is narrower than the first channel portion.

10. The apparatus of claim 9 wherein the second channel portion has a second redirection structure opposite of the first redirection structure to redirect the analyte flow by the sheath flow out of the excitation light from the first detection area.

11. The apparatus of claim 1 wherein flow rate of at least one of the analyte flow and the sheath flow is controlled by a fluid control mechanism.

12. The apparatus of claim 4 wherein flow rate of the bias flow is controlled by a bias control mechanism.

13. A method comprising:
receiving a first excitation light, an analyte flow, and a sheath flow to go through a first channel portion, the analyte flow and the first excitation light being separated while in the first channel portion, the sheath flow flowing on two sides or surrounding the analyte flow; and
redirecting the analyte flow by the sheath flow into the first excitation light at a first detection area using a first redirection structure of a second channel portion.

14. The method of claim 13 wherein redirecting the analyte flow into the first excitation light comprises:
causing the analyte flow to be deflected by the sheath flow into the first excitation light at the first detection area using a first deflection segment connecting a first side of the first channel portion to a first side of the second channel portion.

15. The method of claim 14 wherein redirecting the analyte flow into the first excitation light further comprises:
causing the analyte flow to be deflected by the sheath flow into the first excitation light at the first detection area using the first deflection segment and a second deflection segment connecting a second side of the first channel portion to a second side of the second channel portion.

16. The method of claim 13 wherein redirecting the analyte flow into the first excitation light comprises:
causing the analyte flow to be deflected by the sheath flow into the first excitation light at the first detection area using a bias flow that flows through the second channel portion via a bias port.

17. The method of claim 13 further comprising:
redirecting the analyte flow by the sheath flow into a second excitation light at a second detection area using a third channel portion having a second redirection structure coupled to the second channel portion.

18. The method of claim 17 wherein redirecting the analyte flow into the second excitation light comprises:
causing the analyte flow to be deflected by the sheath flow into the second excitation light at the second detection area using a first deflection segment connecting a first side of the second channel portion to a first side of the third channel portion.

19. The method of claim 18 wherein redirecting the analyte flow into the second excitation light further comprises:
causing the analyte flow to be deflected by the sheath flow into the second excitation light at the second detection area using a second deflection segment connecting a second side of the second channel portion to a second side of the third channel portion.

20. The method of claim 17 wherein redirecting the analyte flow into the second excitation light comprises:
causing the analyte flow to be deflected by the sheath flow into the second excitation light at the second detection area using a bias flow that flows through the third channel portion via a bias port.

21. The method of claim 15 wherein the first and second deflection segments are in opposite directions such that the second channel portion is narrower than the first channel portion.

22. The method of claim 21 further comprising:
redirecting the analyte flow by the sheath flow out of the excitation light from the first detection area using a second redirection structure opposite of the first redirection structure.

23. The method of claim 16 further comprising:
controlling flow rate of the bias flow using a bias control mechanism.

24. A system comprising:
an optical unit to generate at least a light beam of excitation light; and
a flow delivery unit to deliver a sheath flow and an analyte flow; and
a fluidic channel coupled to the flow delivery and optically coupled to the optical unit, the fluidic channel comprising:
a first channel portion receiving a first excitation light of the at least light beam, the analyte flow, and the sheath flow, the analyte flow and the first excitation light being separated while in the first channel portion, the sheath flow flowing on two sides or surrounding the analyte flow, and
a second channel portion having a first redirection structure coupled to the first channel portion to redirect the analyte flow by the sheath flow into the first excitation light at a first detection area.

25. An apparatus comprising:
a first channel portion receiving a first excitation light, an analyte flow, and a sheath flow, the analyte flow and the first excitation light being aligned while in the first channel portion in an area, the sheath flow flowing on two sides or surrounding the analyte flow; and
a second channel portion having a first redirection structure coupled to the first channel portion to redirect the analyte flow by the sheath flow out of the first excitation light away from the area.

* * * * *